United States Patent [19]

Woskov et al.

[11] Patent Number: 5,671,045
[45] Date of Patent: Sep. 23, 1997

[54] MICROWAVE PLASMA MONITORING SYSTEM FOR THE ELEMENTAL COMPOSITION ANALYSIS OF HIGH TEMPERATURE PROCESS STREAMS

[75] Inventors: Paul P. Woskov, Bedford; Daniel R. Cohn, Chestnuthill, both of Mass.; Charles H. Titus, Newtown Square, Pa.; Jeffrey E. Surma, Kennewick, Wash.

[73] Assignee: Masachusetts Institute of Technology, Cambridge, Mass.

[21] Appl. No.: 540,575

[22] Filed: Oct. 6, 1995

Related U.S. Application Data

[63] Continuation-in-part of Ser. No. 141,857, Oct. 22, 1993, Pat. No. 5,479,254.
[51] Int. Cl.$^6$ .................. G01J 3/30; H01P 1/00; G01N 21/69
[52] U.S. Cl. .................. 356/316; 333/99 PL
[58] Field of Search .................. 356/316; 333/99 PL

[56] References Cited

U.S. PATENT DOCUMENTS

| | | |
|---|---|---|
| 3,554,648 | 1/1971 | Boostrom et al. |
| 3,665,182 | 5/1972 | Goff et al. |
| 4,154,000 | 5/1979 | Kramer. |
| 4,341,723 | 7/1982 | Hirosawa. |
| 4,888,295 | 12/1989 | Zaromb et al. |
| 4,933,650 | 6/1990 | Okamoto. |
| 4,965,540 | 10/1990 | Sullivan. |
| 5,014,287 | 5/1991 | Thornton et al. |
| 5,211,142 | 5/1993 | Matthews et al. |
| 5,262,610 | 11/1993 | Huang et al. |
| 5,270,616 | 12/1993 | Itatani. |
| 5,298,751 | 3/1994 | Fee et al. |
| 5,319,437 | 6/1994 | Van Aken et al. |
| 5,376,245 | 12/1994 | McLeod. |
| 5,428,222 | 6/1995 | Alexay. |

FOREIGN PATENT DOCUMENTS

| | | |
|---|---|---|
| 0 397 468 | 11/1990 | European Pat. Off. |
| 4004560 A1 | 8/1990 | Germany. |
| 2 158 608 | 11/1985 | United Kingdom. |
| WO 95/11442 | 4/1995 | WIPO. |

OTHER PUBLICATIONS

Okamoto et al., "High-Power Microwave-Induced Plasma Source for Trace Element Analysis", Japenese Jour. of Applied Physics, vol. 29, No. 4 (Apr. 1990).

Zander, "Atomic Emission Sources for Solution Spectrochemistry", Analytical Chemistry, vol. 58, No. 11 (Sep. 1986).

(List continued on next page.)

*Primary Examiner*—K. Hantis
*Attorney, Agent, or Firm*—Choate, Hall & Stewart

[57] ABSTRACT

Microwave-induced plasma for continuous, real time trace element monitoring under harsh and variable conditions. The sensor includes a source of high power microwave energy and a shorted waveguide made of a microwave conductive, high temperature capability refractory material communicating with the source of the microwave energy to generate a plasma. The high power waveguide is constructed to be robust in a hot, hostile environment. It includes an aperture for the passage of gases to be analyzed and a spectrometer is connected to receive light from the plasma. Provision is made for real time in situ calibration. The spectrometer disperses the light, which is then analyzed by a computer. The sensor is capable of making continuous, real time quantitative measurements of desired elements, such as the heavy metals lead and mercury. The invention may be incorporated into a high temperature process device and implemented in situ for example, such as with a DC graphite electrode plasma arc furnace. The invention further provides a system for the elemental analysis of process streams by removing particulate and/or droplet samples therefrom and entraining such samples in the gas flow which passes through the plasma flame. Introduction of and entraining samples in the gas flow may be facilitated by a suction pump, regulating gas flow, gravity or combinations thereof.

47 Claims, 6 Drawing Sheets

OTHER PUBLICATIONS

Skogerboe et al., "Microwave Plasma Emission Spectrometry", Analytical Chemistry, vol. 48, No. 7 (Jun. 1976).

Taylor et al., "Determination of Trace Impurities in Argon By Microwave Induced Excitation", Analytical Chemistry, vol. 42, No. 8 (Jul. 1970).

Bacharach Instrument Co. (Pittsburgh, Pa.), Produce Description for "J–W Mercury Vapor Sniffer", No. Date.

Barnes et al., "Design Concepts for Stripline Microwave Spectro Chemcial Sources", Anal. Chem., vol. 62, No. 23, Dec. 1, 1990, pp. 2650–2654.

Beenakker et al., "An Assessment of a Microwave–Induced Plasma . . . Solutions", Spectrochimica Acta, vol. 33, pp. 373–381, 1978.

M.W. Blades et al., "Application of Weakly Ionized Plasmas for Materials Sampling and Analysis", IEEE Trans. on Plasma Sci., vol. 19, pp. 1090–1113, 1991.

Demirgian, "Continuous Emission Monitor for Incinerators", U.S. Depart. of Energy Info. Exchange Meeting on the Characterization, Monitoring and Sensor Technologies, Dallas, Texas, Jun. 3–4, 1992.

F.C. Fehsenfeld et al., "Microwave Discharge Cavities Operating at 2450 MHz", Rev. of Sci. Instm., vol. 36, pp. 294–298, 1965.

K.A. Forbes et al., "Comparison of Microwave–Induced Plasma Sources, J. of Analytical Atomic Spectrometry", vol. 6, pp. 57–71, 1991.

Goode et al., "A Review of Instrumentation Used to Generate Microwave–Induced Plasmas", Applied Spectroscopy, vol. 38, No. 6, Nov.–Dec./1984 pp. 755–763.

T. Ishizuka et al., "Atomic Emission Spectrometry of Solid Samples with Laser Vaporization–Microwave Induced Plasma System", Anal. Chem., vol. 52, pp. 125–129, 1980.

J.P. Matousek et al., "Microwave–Induced Plasmas: Implementation and Application", Prog. Analyt. Atom. Spectrosc., vol. 7, pp. 275–314, 1984.

H. Matusiewicz, "A Novel Microwave Plasma Cavity Assembly for Atomic Emission Spectrometry", Spectrachimica Acta., vol. 47B, pp. 1221–1227, 1992.

Y. Okamoto, "Annular–Shaped Microwave–Induced Nitrogen Plasma at Atmospheric Pressure for Emission Spectrometry of Solutions", Analytical Sciences, vol. 7, pp. 283–288, 1991.

Pacific Northwest Laboratory, Technology Brief for "Spectrochemical Emission Sensor".

D.K. Smith et al., "Microwave Atmospheric Pressure Plasma Torch, Characteristics and Application", 27th Microwave Symposium, Washington, D.C., Aug. 2–5, 1992.

A.T. Zander et al., "Microwave–Supported Discharges", Applied Spectrosc., vol. 35, pp. 357–371, 1981.

Mark II Exhaust Spectrum with High-Resolution Spectrometer just Prior to Start of Soil Loading. Slag Temperature 1410 °C

FIG. 7

Partial Time Record of Chromium Emissions and Slag Temperature in the Mark II Furnace During Soil Loading

MICROWAVE PLASMA MONITORING SYSTEM FOR THE ELEMENTAL COMPOSITION ANALYSIS OF HIGH TEMPERATURE PROCESS STREAMS

CROSS-REFERENCE TO RELATED APPLICATION

This application is a continuation-in-part application of U.S. Ser. No. 08/141,857, filed Oct. 22, 1993, now U.S. Pat. No. 5,479,254, the entire contents of which are incorporated herein by reference.

This invention was made with government support under MIT subcontract Number 154462-A-L2 with Battelle Laboratories (under DOE Prime Contract Number DE-AC06-76RLO 1830) The government has certain rights in the invention.

TECHNICAL FIELD

This invention relates to method and apparatus for analyzing elemental compositions of process streams, and more particularly to method and apparatus for continuous, real time monitoring of the elemental content of gas, solid and/or liquid material streams entering and exiting furnaces using a microwave-induced plasma and atomic emission spectroscopy which could be implemented in a high temperature environment in situ or in close proximity thereto.

BACKGROUND OF THE INVENTION

In the global effort to protect the environment, there exists the need to monitor exhaust gases from all types of furnaces to detect the emission of hazardous chemicals. Strictly controlling furnace off-gas emissions is important because such gases pose an unacceptable safety and health risk on local communities and the environment. It is desirable that such a monitoring device be capable of continuous, real time emission diagnostics of vapors and particulates in furnace streams under harsh and variable conditions. In particular, location in situ or close proximity in the furnace off-gas stream would facilitate accurate spatially resolved measurements. It is also desirable that such a monitoring device be able readily to detect the presence of hazardous elements, such as trace metals including lead (Pb), mercury (Hg), arsenic (Ar), beryllium (Be), chromium (Cr), antimony (Sb), barium (Ba), cadmium (Cd), thallium (Tl), nickel (Ni), selenium (Se), and silver (Ag) as soon as they appear in the exhaust gas and at levels below Environmental Protection Agency mandated threshold levels. Such a device must also be useable in or in close proximity to the hot, dirty environment of a furnace and be capable of detecting the presence of many different elements simultaneously.

Instrumentation for the sensitive analysis of materials developed to date suffer from limitations including their not being true continuous, real time devices, not applicable to in situ measurements, not capable of detecting trace metals, or being limited to monitoring only one element at a time. The use of plasma sources for elemental excitation or detection is currently the primary means for detection of trace elements in solids, liquids and gasses. Blades et al, Application of Weakly Ionized Plasmas for Materials Sampling and Analysis, *IEEE Trans. on Plasma Sci.*, Vol. 19, pp. 1090–1113 (1991), have reviewed such technology, which included conductively coupled plasmas, microwave-induced plasmas, and other techniques. None of the techniques so described are applicable to continuous, real time in situ measurements. Fast Fourier transform spectroscopy, as described by J. Demirgian, *Continuous Monitor for Incinerators*, U.S. Department of Energy Information Exchange Meeting on the Characterization, Monitoring, and Sensor Technologies, Dallas, Tex. (Jun. 3–4, 1992), can be used for continuous, near real time monitoring of molecular gases, but is not capable of the detection of metals, especially if the metals are in particulate form. Commercial in situ detectors, such as the Bacharach Instrument Company mercury sniffer model MV-2J-W and the Pacific Northwest Laboratory Halo-sniff spectrochemical emission sensor are limited to detecting only one element at a time. Further, these devices cannot be used for continuous, real time measurements of metals in a wide range of particulate as well as vapor form in a furnace environment. They must pull in a gas sample through a pipe and/or small orifice, which if used in a hot exhaust environment could give false results due to condensation or blockage due to larger particulate.

Fehsenfeld et al, Microwave Discharge Cavities Operating at 2450 MHZ, *Rev. of Sci. Instrm.*, Vol. 36, pp. 294–298 (1965), described a number of microwave-induced plasma (MIP) resonator cavity structures. One such structure had a built in taper to reduce its height to increase the electric field strength for plasma breakdown. This device was a resonator, not a shorted waveguide. It also included a number of features that limited maximum microwave power, such as a cable connection to the source of such power. None of the devices described by Fehsenfeld can be used in a furnace environment. Barnes et al, Design Concepts for Strip-Line Microwave Spectrochemical Sources, *Anal. Chem.*, Vol. 62, pp. 2650–2654 (1990), described a shorted strip-line microwave MIP arrangement with a dielectric tube through the device one-quarter wavelength from the shorted end. Again, the features of this device, such as the presence of the strip-line and the cable connection to the source, would limit the maximum power operation of this device. Furthermore, this device could not be used in the hot, dirty furnace exhaust environment.

Matusiewicz, A Novel Microwave Plasma Cavity Assembly for Atomic Emission Spectrometry, *Spectrachimica Acta*, Vol. 47B, pp. 1221–1227 (1992); Okamoto, Annular-Shaped Microwave-Induced Nitrogen Plasma at Atmospheric Pressure for Emission Spectrometry of Solutions, *Analytical Science*, Vol. 7, pp. 283–288 (1991); and Smith et al, Microwave Atmospheric Pressure Plasma Torch, Characteristics and Application, 27th *Microwave Symposium*, Washington, D.C. (Aug. 2–5, 1992), described higher power MIP devices connected to the microwave source directly by waveguide. These devices utilize dielectric tubes and lack the provision for remote calibration, ignition or heating, which make them unsuitable for use in a furnace environment.

Other microwave-induced plasma-atomic emission spectroscopy devices are described by Forbes et al, Comparison of Microwave-induced Plasma Sources, *J. of Analytical Atomic Spectrometry*, Vol. 6, pp. 57–71 (1991); Matousek et al, Microwave-Induced Plasmas: Implementation and Application, *Prog. Analyt. Atom. Spectrosc.*, Vol. 7, pp. 275–314 (1984); Goode et al, A Review of Instrumentation Used to Generate Microwave-Induced Plasmas, *Applied Spectrosc.*, Vol. 38, pp. 755–763 (1984); and Zander et al, Microwave-Supported Discharges, *Applied Spectrosc.*, Vol. 35, pp. 357–371 (1981).

Real time, remote calibration is also an important feature for any continuous, real time MIP device which must operate over a variable range of gas flow composition. A furnace off-gas stream will consist of the main working gas, such as air or nitrogen, along with a variable and not-well characterized waste off-gas. Atomic emission line intensities depend, in part, on the plasma gas mixture (matrix effect). This makes in situ calibration necessary for quantitative measurements. The use of laser ablation to introduce samples for calibration purposes into an MIP device has been described by Ishizuka et al, Atomic Emission Spectrometry of Solid Samples with Laser Vaporization-Microwave Induced Plasma System, *Anal. Chem.*, Vol. 52, pp. 125–129 (1980). However, this device would not work for remote calibration because an absolute calibration is required, not the relative one for which the Ishizuka et al device was designed. In the Ishizuka et al device, tubing between the laser ablation plate and the plasma causes much of the laser sputtered material to condense out making an absolute calibration unreliable. In addition, particulates are not directly volatilized. D'Silva et al, Remote Real-Time Analysis of Hazardous Wastes Through Laser Ablation-Inductively Coupled Plasma Atomic Emission Spectrometry, *Proceedings of the Information Exchange Meeting on Characterization, Sensors, and Monitoring Technologies,* Dallas, Tex. (Jul. 15–16, 1992), disclose using laser ablation to ablate solid material into the gas stream of an inductively coupled plasma (ICP) for atomic emission spectroscopy. The apparatus described in D'Silva et al utilizes laser ablation with an ICP for analytical characterization of soil composition. An ICP, however, is not sufficiently robust for an ambient gas environment. In addition, large flows of argon gas are continuously required in the instrument described by D'Silva et al.

It therefore would be desirable to provide method and apparatus which overcome the shortcomings associated with the prior art.

SUMMARY OF THE INVENTION

The microwave-induced plasma element sensor according to the invention includes a source of microwave energy and a shorted waveguide made of a microwave conductive material, which may be a poor DC electrical conductor, communicating with the source of the microwave energy to generate a plasma. The waveguide includes an aperture for the passage of the gasses to be analyzed and a spectrometer is connected to receive light from the plasma. The spectrometer analyzes the received light spectrum to identify elements. In a preferred embodiment, the potion of the waveguide exposed to the furnace gasses is made of refractory material and may be an open mesh. Provision can be made to heat this portion of the waveguide in addition to the microwave power absorption in the waveguide to prevent furnace gas condensation. This embodiment includes a retractable ignitor for igniting the plasma or reigniting it, if necessary during operation. A calibration apparatus is provided to perform an absolute calibration so that quantitative measurements can be made. It is also preferred that structure be included to provide a source of electrons and/or to create turbulence in the plasma which helps to localize the plasma in the waveguide where plasma operation is optimized. The waveguide may also include impedance matching. It is also preferred that the waveguide be tapered to intensify further the electric field to aid plasma breakdown. It is preferred that the refractory material be graphite or molybdenum and the refractory may be lined or coated with non-oxidizing materials for operation in a hot oxidizing environment. The spectrometer may be a Czerny-Turner grating spectrometer. Fiber optics are preferred for transmission of the plasma light to the spectrometer. For in situ operation the fiber optics would be unclad quartz or equivalent optical/ untransmitting, high temperature material for robustness in a hot environment.

In one embodiment of the invention, the calibration system includes an alloy plate including elements of interest and a laser having a power selected to eject known masses of material for calibration purposes. In the preferred embodiment, the laser beam is transmitted by fiber optics to the calibration plate. Alternative remote calibration configurations include the use of electric sparks, aerosols or gaseous calibration sources.

The sensor of the present invention is well-suited to real time in situ operation in that the refractory materials and robust fiber optics can operate in the hostile environment of the furnace exhaust gases. The present configuration does not require a continuous, gas tight dielectric tube through the device to confine the gas flow in the plasma, as required in prior art MIP devices. Such tubes without openings for optics are typically made of quartz, boron nitride or other high temperature non-microwave absorbing materials and are detrimental in an in situ device since they are subject to clouding (blocking the plasma light) in a dirty furnace off-gas environment.

In an alternative embodiment of the invention, a system is provided that uses a high-power microwave sustained plasma for atomic emission spectroscopy for elemental analysis of material process streams by entraining particulate and/or droplet samples from the process stream in a gas flow which passes through the plasma time. This embodiment of the invention includes a plasma torch, a real time sample acquisition subsystem, a spectrometer subsystem and a high power microwave source which provides power for sustaining the plasma. The spectrometer subsystem is utilized to detect and analyze the plasma light emission of the particulate or droplet samples.

The plasma torch in this embodiment is designed to operate at high power, e.g. greater than 500 Watts, and at near atmospheric pressure. The plasma torch also operates on ambient air or other ambient gas of the process being monitored. This is accomplished using a suction pump and/or gravity to draw sample particulate and/or droplets through the plasma for analysis. One such pump which is suitable for use in accordance with the present invention is a Penberthy jet pump. In a preferred embodiment, the microwave plasma torch also includes a start-up system with a source of start-up gas, such as argon, that easily breaks down to initiate an electric discharge.

The plasma is positioned in a shorted waveguide. The waveguide includes an aperture for the passage of the gasses, particulates and/or droplets to be analyzed and a spectrometer is connected to receive light from the plasma. The plasma or gas flow passage is transverse to the waveguide direction for microwave power propagation. As mentioned above, a suction pump may be employed to draw the gas stream with particulate material and/or droplets to be analyzed through the waveguide, preferably from top to bottom.

A start-up and sustainer tube is positioned in the center of the gas flow with its end aligned approximately with the inside waveguide wall. In a preferred embodiment, the gas flow enters a passage near the top of the waveguide. Preferably, the start-up and sustainer tube is formed of a dielectric material that is capable of withstanding high temperatures, such as alumina or boron nitride. When the end of the start-up and sustainer tube is heated by the plasma, the end of the tube acts as an electron emitter to sustain and center the plasma in the flow through the waveguide.

A start-up wire, such as a tungsten wire, is positioned within the start-up and sustainer tube and is connected to a high voltage power supply, such as telsa coil. Preferably, the start-up wire is recessed a sufficient distance from the inside waveguide wall to avoid directly coupling to the microwave power inside the waveguide. The high voltage power supply is momentarily activated to cream a discharge at the end of the start-up tube which provides the initial free electrons for start-up of the main microwave plasma torch. The start-up and sustainer tube preferably is connected to a source of auxiliary gas, such as argon, through a valve or the like that can also be momentarily opened to facilitate the initiation of the main plasma torch.

A debris trap and a clean out port for collecting and removing large particles that are not volatilized by the plasma and bits of the sustainer tube which could fracture is positioned downstream of the plasma flow. Preferably, the plasma flow is in a downward direction and the debris trap is positioned on the bottom side of the waveguide. While the orientation of the plasma flame is not critical, the vertical flame down arrangement reduces or eliminates the accumulation of debris and facilitates the debris trap and clean out port feature of the present invention. The suction pump preferably is offset to one side of the axis of the plasma flame.

The present invention further provides an efficient sample introduction arrangement that utilities suction and/or gravity to facilitate sample entrainment into the plasma flow. For example, sufficiently small particulate and/or droplet samples can be introduced into the microwave plasma torch system through a sample insertion tube positioned proximate to the start-up and sustainer tube. In this embodiment, gravity and gas flow both act to entrain particles in the plasma flame. Alternatively, particulate and/or droplet samples can be introduced into the microwave plasma torch system using the suction pump to pull the samples into the main gas flow and through the plasma. A valve or the like may be utilized to control plasma gas flow and the degree of suction that is achieved in the suction tube for sample acquisition. Preferably, a large particle trap is positioned below the suction tube, thereby allowing large particles to fall out of or be removed from the gas flow prior to passage through the plasma flame.

For either of the above-described methods of sample introduction, the microwave power is sufficiently high such that small particulate and/or droplets are volatilized, compounds are broken down into elements, and the atoms excited to emission. Fiber optic guides are imbedded in the waveguide and positioned to transmit the atomic emission light to a spectrometer system.

The microwave plasma torch provided by this embodiment of the invention facilitates absolute calibration for the mass of each element species passing through the plasma flame. Absolute calibration is achieved by dropping a predetermined amount of powder of known element masses through the sample insertion tube. The short vertical drop insures that all the calibration mass passes through the flame. The fiber optic guides positioned along the flow of the flame allow the determination of the rate of mass flow by time of flight measurement of the calibration mass transient through the flame. Finally, any unvolatilized calibration particulates are collected on the clean out port flange and can be weighed to account for the fraction of the calibration mass that was not volatilized. Relative calibration can be achieved by injecting a calibrated aerosol spray into the plasma gas flow.

The present invention also includes a sample acquisition subsystem or subsystems. The sample acquisition subsystems provide a continuous, real time flow of samples from the process material stream or streams to be monitored. Samples can be acquired using a variety of techniques. For example, a sample scraper is utilized to scratch the surface of the material stream as it moves by and/or as the scraper arm is articulated. The resulting small particulates scraped from the material stream fall into a grinder/pulverizer machine which converts the samples into a fine powder. A fine mesh strainer preferably is employed to select a maximum particle size which is dropped down through a feed tube into the plasma torch. Alternatively, a sample impactor is positioned near the material stream and the suction input to the plasma torch. The sample impactor creates and knocks from the material stream small particles or droplets that are then entrained in the gas flow stream through the plasma torch by the suction action. The sample impactor could be a repetitively pulsed rod in a solenoid, a repetitively pulsed high pressure gas jet or the like. Other sample acquisition techniques suitable for use in accordance with the invention include, but are not limited to, a high energy laser beam or electric spark discharges to ablate or fracture samples from the process stream into the plasma torch.

The design of the microwave plasma monitoring system in accordance with the present invention is very robust and allows the plasma torch to be positioned very near or proximate to the process stream to be monitored, thereby minimizing sample transport losses. Additionally, it is not necessary that the plasma torch be located below the monitored process stream. A sample acquisition subsystem that lifts the sample a short distance to drop the sample through the plasma flame may be readily adapted for use in the present invention. The foregoing has outlined some of the more pertinent objects of the present invention. These objects should be construed to be merely illustrative of some of the more prominent features and applications of the invention. Many other beneficial results can be attained by applying the disclosed invention in a different manner of modifying the invention as will be described. Accordingly, other objects and a fuller understanding of the invention may be had by referring to the following Description of the Preferred Embodiment.

BRIEF DESCRIPTION OF THE DRAWINGS

For a fuller understanding of the present invention, reference is had to the following description taken in conjunction with the accompanying drawings, in which.

DESCRIPTION OF THE PREFERRED EMBODIMENT

Figure 1:
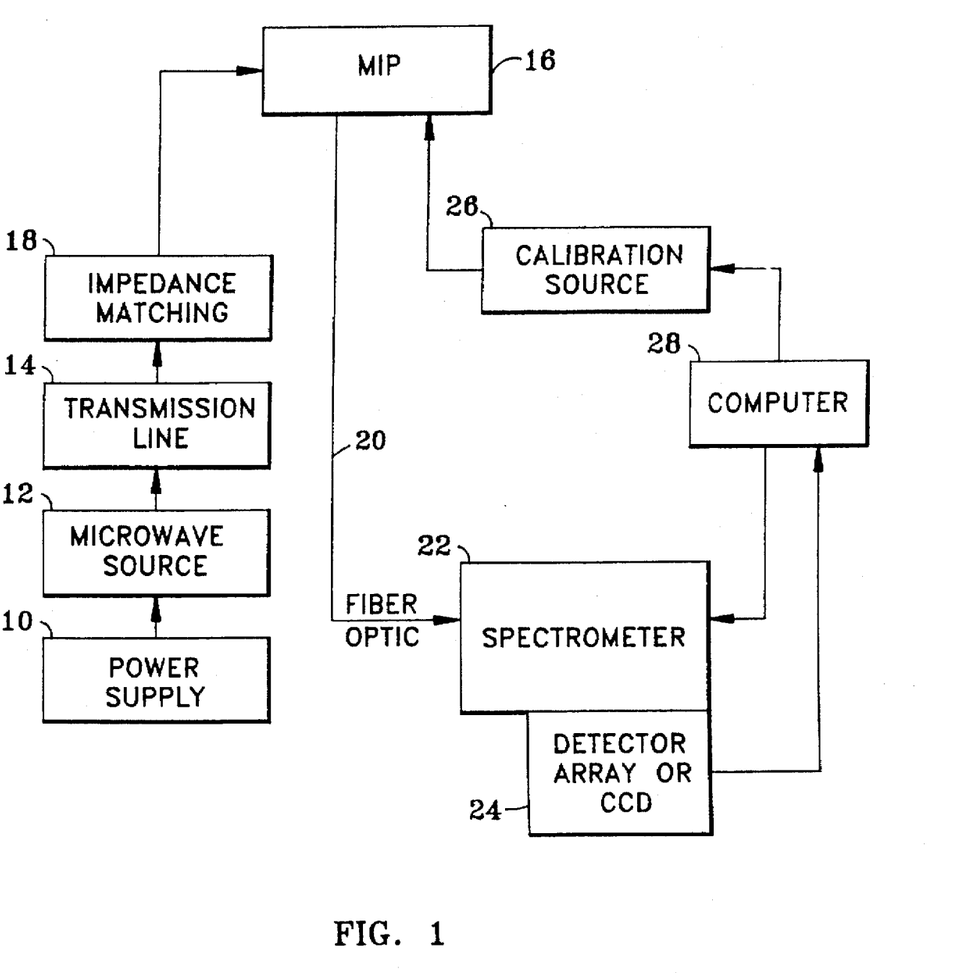
FIG. 1 is a block diagram of the microwave-induced plasma-atomic emission spectroscopy element analysis system of the invention.

FIG. 1 illustrates the major components of a microwave induced plasma—atomic emission spectroscopy element analysis system in accordance with the present invention. A power supply 10 powers a microwave source 12 with output powers greater than 300 Watts. An example of such a source is a magnetron. The high power level of the present invention is an advantage for robust operation in an in situ environment with variable gas mixes. The output of the microwave source 12 is transmitted by a transmission line 14 such as a waveguide to the plasma 16 through an impedance matching device 18. An impedance matching device may be a triple stub or an E-H tuner. An impedance matching device provides maximum transfer of energy from the source to the load by minimizing reflection and distortion. The source output interacts with the plasma support gas, such as air or nitrogen, which flows upstream through the transmission line creating plasmas which are ionized gas molecules and electrons. Plasmas, in turn, interact with particulates, compounds and atoms in the off-gas stream and produce excited atoms. As the excited atoms decay, plasma light is emitted. The emitted plasma light which spans from the ultraviolet (180 nm) through near infrared (2000 nm) is transmitted by a fiber optic cable 20 to a spectrometer 22 such as a Czerny Turner grating configuration. A detector array 24 such as a silicon linear diode array or a charge coupled device array is used to instantaneously detect the dispersed plasma spectrum over a part of the plasma light spectrum. The part of the plasma spectrum that can be instantaneously detected depends on the dispersion of the spectrometer and the size of the detector array. For example, a 0.62 m Czerny Turner grating spectrometer with a 2400 groove/mm grating and a 512 diode detector array will instantaneously detect approximately a 6.5 nm spectral band with 0.01 nm resolution. The grating can be rotated to access other portions of the spectrum. A calibration source 26 which can inject a known quantity of elements to be monitored is used to calibrate the emission levels for quantitative measurements. A computer 28 acquires the detector array data, controls the spectrometer tuning, and operates the calibration source.

Figure 2:
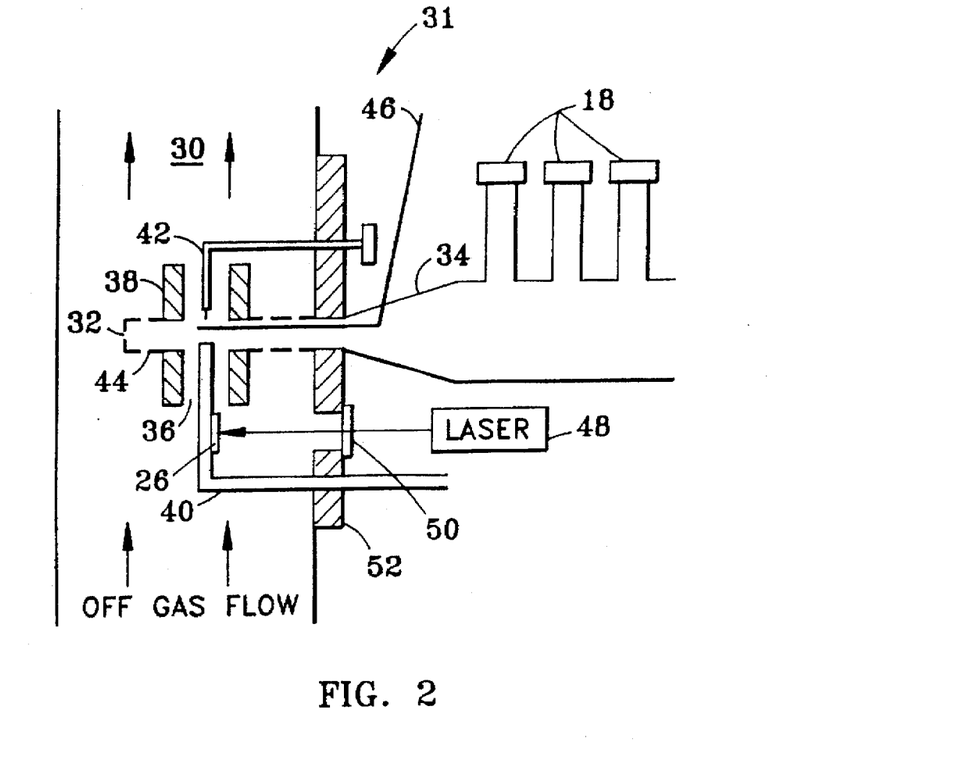
FIG. 2 is a side view of the apparatus of the invention.
Figure 3:
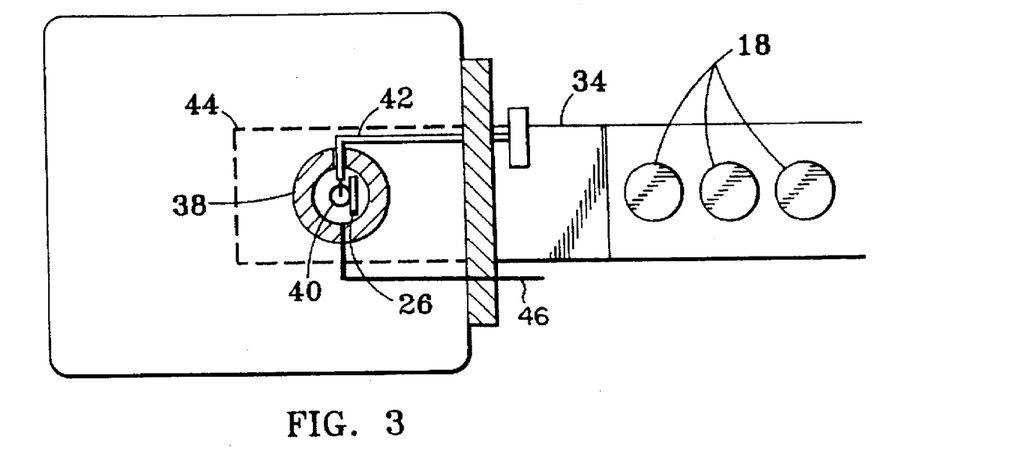
FIG. 3 is a top view of the apparatus of the invention.

FIGS. 2 and 3 illustrate details of the microwave induced plasma element sensor 31 according to the invention. The sensor is placed in an off-gas flow stream 30 of a furnace (not shown). As discussed above, output from the microwave source 12 transmits through the waveguide 14 via an impedance matching device 18. The waveguide 14 is tapered 34 and shorted at one end 32. The plasma is created inside the shorted waveguide wherein the standing wave electric field is peaked at a distance $\frac{1}{4} \lambda_g$ from the shorted end 32 of the waveguide 14, where $\lambda_g$ is the guide wavelength for the microwave source power. To further intensify the electric field for plasma breakdown, the height of the waveguide is reduced relative to the transmitting waveguide through the waveguide taper 34. However, it is also possible to operate this plasma without a reduced waveguide. The direction of the electric field is parallel to the waveguide short wall dimension, which is also the direction of the gas flow 30 through the guide. A passageway 36 through the waveguide walls at the plasma location allows for a clear flow of the gases through the plasma region and removes solid material contact with the plasma. The aperture of the passageway 36 is less than $\frac{1}{4} \lambda_o$, where $\lambda_o$ is the free space wavelength of the microwave source power. Tubular structures 38 made of a microwave conducting material extend outward beyond the passageway 36 in both directions. These tubes 38 localize the gas flow through the plasma region and act as cutoff waveguides to prevent microwave leakage. The tube is constructed from refractory conductor material such as graphite, molybdenum or other suitable material. The MIP sensor structure 31 can be placed in a hot hostile furnace environment as a result of using a refractory material. To be used in a hot, oxidizing environment, the material could be lined or coated with non-oxidizing materials. In addition, the use of refractory materials along with the placement in a flowing gas stream makes optional the need for a quartz, boron nitride, or other high temperature, non-microwave absorbing tube inserted completely through the microwave structure which is a feature of all other prior art MIP devices. The dielectric tube without openings for optics in prior art MIP devices is detrimental to an in situ device because it is subject to clouding in a dirty furnace off-gas environment.

An obstruction such as an alumina tube 40 inserted into the waveguide through the passageway 36 on the input gas flow side of the guide 14 acts as an electron emitter and creates turbulence in the gas flow which additionally localizes the plasma in the center of the passageway 36. A retractable ignitor 42 is inserted through the upper part of the passageway 36 to initiate plasma breakdown when the microwave power is first turned on or if the plasma goes out during operation. When the plasma is on, this ignitor is retracted or rotated out of the way. In this embodiment, the retractable ignitor is an insulating rod such as alumina with a short length of wire at its tip. The wire acts as an antenna and concentrates the electric field. Other remote ignition techniques are also possible such as an electric or laser spark.

It is preferred that the waveguide 14 which is within the gas stream 30 be made from an open mesh or an aerodynamically streamlined solid walled waveguide 44. The open mesh 44 configuration or aerodynamic streamlining configuration reduces blockage of the off gas stream flow. In addition, a mesh configuration allows more flexibility for viewing plasma emission light. The open mesh 44 is also made of a refractory material such as graphite, molybdenum or tungsten wire. A fiber optic 46 attached to the outside of the waveguide 14 in the vicinity of the plasma transmits the emission light to the spectrometer 22 (FIG. 1). However, a closed waveguide with an appropriate hole or holes for the fiber optic can also be used.

The present invention also includes the provision for remote calibration. This is an important feature for a continuous, real time MIP device which must operate over a variable range of gas flow compositions. A furnace off gas stream consists of the main working gas such as air or nitrogen along with a waste off gas that is variable and not well characterized. As atomic emission line intensities depend, in part, on the plasma gas mixture, in situ calibration is necessary for precise quantitative measurements. In a preferred embodiment, calibration is provided by a laser 48 which ablates a solid plate 26 with a known mix of elements to be analyzed. This plate may be an alloy of heavy metals. The plate is located on the gas input side of the waveguide 14 as close as possible to the plasma. A laser beam is focused onto the plate through a window 50 on the MIP element sensor mounting flange 52 to eject an amount of material which is determined in advance. The ablation laser 48 can be pulsed as often as needed to maintain the MIP sensor calibration. Although remote calibration is described in terms of free space propagation laser ablation, an alternative remote calibration configuration such as the use of fiber optics to bring in the laser beam, the use of electric sparks, and aerosol or gaseous calibration sources directed into the plasma through the alumina tube may also be used.

Figure 4:
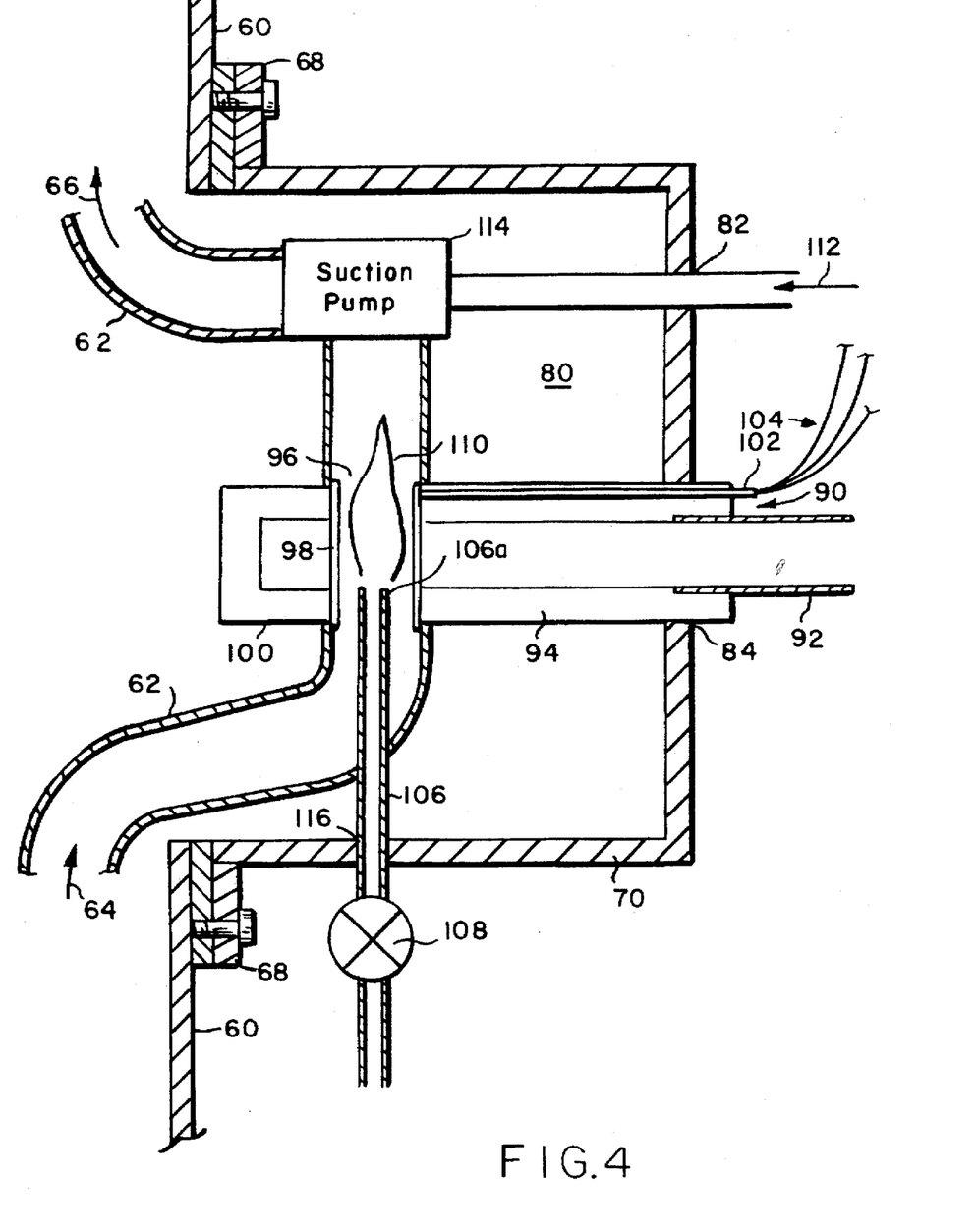
FIG. 4 is a side view of an alternative embodiment of the apparatus in accordance with invention.

Referring now to FIG. 4, the microwave plasma and waveguide device may be located as part of the furnace exhaust duct 60 structure positioned in close proximity to the furnace upstream of the exhaust gas scrubbers. In one embodiment of the invention, the device is located with the exhaust gas input 64 about one meter from the furnace. As also shown in FIG. 4, the furnace exhaust stream is intercepted by tube 62 which is bent into the center of the furnace exhaust duct 60. The tube 62 may be formed of stainless steel or the like which will survive the high temperature environment and not introduce impurities of the elements to be monitored. The exhaust stream sample enters exhaust input 64, undiluted and at high temperature, passes through the plasma flame 110 and is returned to the furnace exhaust through exhaust return 66. A suction pump 114, such as a Penberthy jet pump, preferably is employed downstream of the plasma 110 to insure that an adequate gas flow is maintained through the waveguide. This is accomplished using a source of gas 112. The nominal gas flow through the waveguide may be in the range of 10–30 l/m (20–60 scfh).

The device 80 according to the invention is mounted to the furnace exhaust 60 using mounting flange(s) 68 or the like. Preferably, device 80 is contained within a gas tight enclosure 70 which forms pan of the exhaust duct 60 wall to prevent exhaust gas leakage. Enclosure 70 may contain several ports or apertures, such as gas entry port 82, waveguide entry port 84, and dielectric tube port 116. Ports in enclosure 70 are appropriately sealed to prevent leakage.

As further shown in FIG. 4, a microwave plasma torch device constructed of refractory materials may be implemented as pan of the furnace exhaust duct to sample high temperature, greater than 500° C., undiluted exhaust gases. For example, the device may be mounted to the side of a Mark II furnace. As used herein, a Mark II furnace refers to a DC graphite electrode plasma are furnace. It should be appreciated, however, that this invention is suitable for use with other furnaces. It is preferred that the device be implemented up stream of the scrubbers (not shown in FIG. 4). This arrangement has proven to be a robust gas excitation device for sensitive in situ atomic emission spectroscopy (in the pan per billion range) of metals entrained in the exhaust emissions (see e.g., Example 1, and FIGS. 6 and 7). The microwave plasma device for atomic emission spectroscopy of the furnace emissions can use, for example, a 1.5 kW, 2.45 GHz magnetron source.

The plasma 110 is induced inside a waveguide 90 which propagates the microwave power to the plasma from the magnetron. Preferably, waveguide 90 is a shorted waveguide 100. Waveguide 90 may be formed partially of metal 92 and partially of graphite 94, as shown in FIG. 4. The graphite portion of waveguide 90 allows the in situ placement of the device relative to the exhaust duct 60. A passageway 96 through the waveguide walls at the plasma location provides a clear flow for the gases, particulates and/or droplets through the plasma region. The aperture of the passageway 96 is less than $\frac{1}{4}\lambda_o$, where $\lambda_o$ is the free space wavelength of the microwave source power. Tubular structures 62 made of a microwave conducting material extend outward beyond the passageway 96 in both directions. These tubes 62 localize the gas flow through the plasma region and act as cutoff waveguides to prevent microwave leakage. The tubes are constructed from high temperature conductor material such as stainless steel, graphite, molybdenum or other suitable material which will not contaminate the measurements. A dielectric liner 98 perforated for fiber optics 104 access 102, is used inside the waveguide to direct the gas flow. Dielectric liner 98 may be formed of boron nitride or the like.

A dielectric tube 106, such as alumina, penetrates the exhaust pick off tube to the waveguide wall, centered in the hole through the guide. The end of this alumina tube 106a provides a thermal source of electrons when heated by the plasma to keep the plasma centered in the gas flow through the guide. This tube also provides a way in which to introduce starter and calibration samples into the plasma. Valve 108 may be positioned on or near tube 106 to control flow and seal the exhaust duct when dielectric tube 106 is not in use. Fiber optic guides 104 may be embedded in a tube 102 in the wall of waveguide 90 as illustrated in FIG. 4. Fiber optic guides 104 transmit the plasma light to the spectrometer (not shown in FIG. 4). For example, fused quartz fiber guides with high temperature gold cladding from Fiberguide Industries may be utilized to transmit the plasma light to the spectrometers. These fibers may be embedded inside the graphite waveguide wall in an alumina tube and could be readily replaced during furnace operation. The fibers 104 preferably penetrate the liner 98 so that the fiber ends are in close proximity to the inside wall of the tube 98. The viewing fends of theses fibers are maintained clean by the radiated plasma heat and the rapid gas flow. Test results using the embodiment of the invention illustrated in FIG. 4 are set forth in detail in Example 1.

The present invention also provides a system for continuous, real time compositional analysis of solid and liquid material streams entering and exiting furnaces. This embodiment may be implemented and utilized in conjunction with furnaces for various processes. For example and while not intended to be construed as limiting, compositional analysis and monitoring of solid and liquid material streams entering and exiting furnaces may be determined in furnaces used for waste processing, materials manufacturing, and power production. In addition, compositional analysis and monitoring of streams is not limited to exhaust streams. Fuel, ash and other streams associated with furnace processes may be analyzed and monitored. The ability to analyze and monitor such process streams in accordance with the present invention is essential for providing real time control of the furnace process such that the process can be run optimally to produce the desired product, maximize efficiency and minimize environmental pollution.

Figure 5:
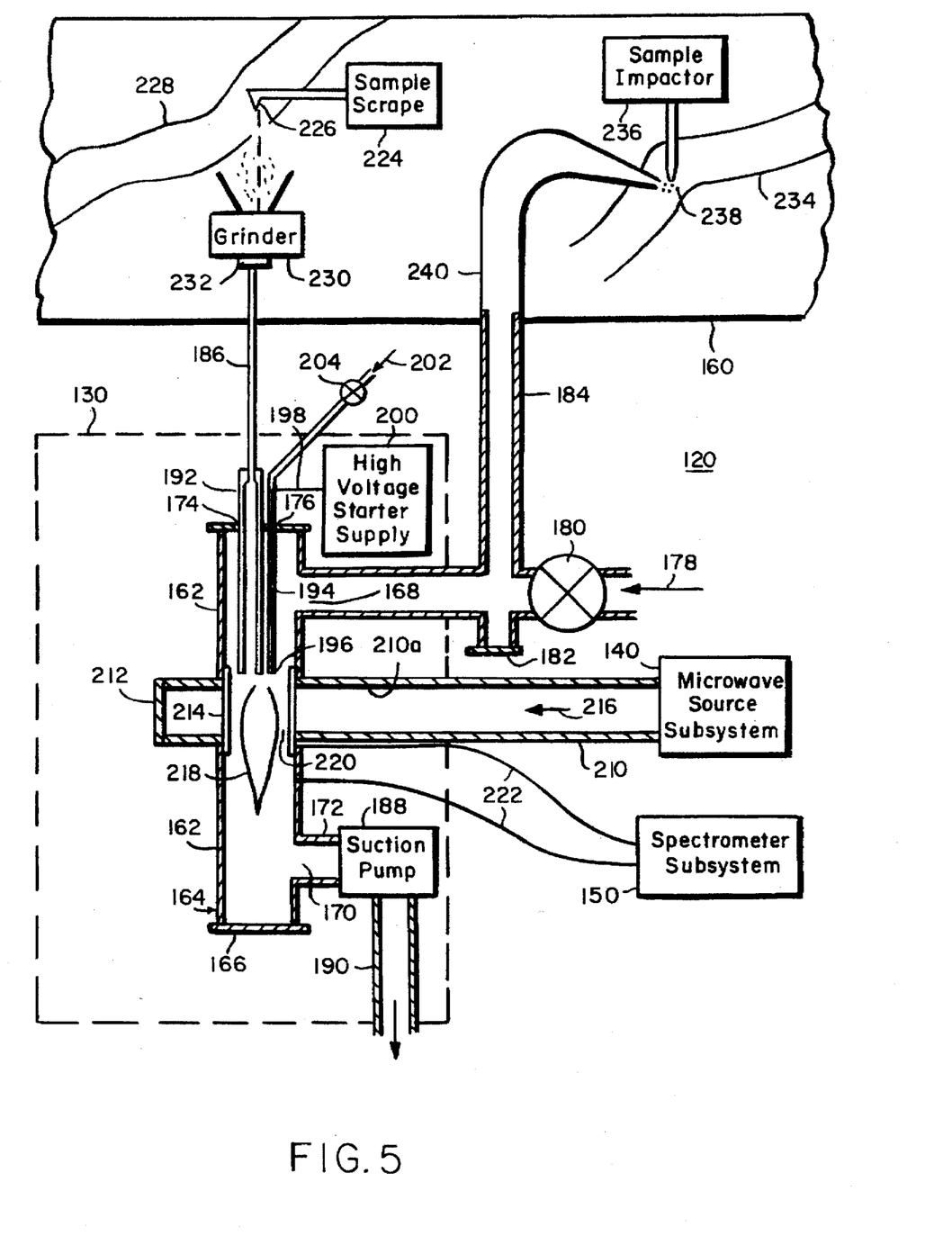
FIG. 5 is a side view of a real time microwave plasma monitoring system for the elemental analysis of material process streams in accordance with another alternative embodiment of the invention.

Referring now to FIG. 5, a system 120 for compositional analysis and monitoring of solid and liquid material streams entering and exiting furnaces and other process streams is shown. As discussed herein, particulates and/or droplets are removed from a process stream containing solid and/or liquid material to be analyzed and are transported through several subsystems. System 120 includes plasma torch subsystem 130, microwave source subsystem 140, spectrometer subsystem 150 and sample acquisition subsystem 160. Preferably, system 120 will contain a start-up subsystem. The plasma torch is designed to operate at high power, e.g. greater than 500 Watts, and at near atmospheric pressure. As described herein, this can be accomplished using a suction pump and/or gravity to draw sample particulate and/or droplets through the plasma for analysis.

Plasma torch subsystem 130 includes sample flow tube 162, which may be formed of stainless steel. It should be appreciated, however, that the material of construction of sample flow tube 162 may vary depending on the application an&or materials being processed. As shown in FIG. 5, sample flow tube 162 contains a plurality of ports or openings. For example, sample flow tube 162 may contain gas flow inlet 168, gas flow outlet 170 and sample insertion port 174. Sample flow tube 162 also may contain clean out port 166 and start-up tube port 176.

As discussed in greater detail herein, a source of sample gas 178 is provided to sample flow tube 162. The flow of sample gas 178, which entrains particulates and/or droplets to be analyzed, may be controlled using a variety of methods. For example and as shown in FIG. 5, valve 180 positioned proximate to the source of sample gas 178 may be used in conjunction with suction pump 188 and/or gravity to regulate the flow of sample gas 178.

A sample to be analyzed is combined with sample gas 178 using sample acquisition subsystem 160. Preferably, the sample to be analyzed is in the form of particulates and/or droplets which becomes entrained in sample gas 178. Small particulates, e.g. <100 μm in cross-section, and/or droplets are combined with sample gas 178 using feed tube 186 and/or sample insertion tube 192. Alternatively, particulates and/or droplets are combined with sample gas 178 using suction tube 184. The latter embodiment is particularly advantageous when larger particulates and/or droplets are to be analyzed. In a preferred embodiment, a large particle trap 182 is provided such that large particles from a process stream 234 are removed prior to passing through sample flow tube 162. The sample gas 178 containing the sample to be analyzed therein passes through plasma 218 and thereafter exits sample flow tube 162 through gas flow outlet 170. Preferably, sample flow tube 162 is capable of having debris and the like removed from the sample flow gas prior to passing through pump 188. This may be accomplished by a debris trap 164 or the like and clean out port 166. While the orientation of the plasma flame is not critical, the vertical flame down arrangement facilitates powdered sample introduction, reduces or eliminates the accumulation of debris at the plasma location, and facilitates the debris trap and clean out port feature of the present invention.

Suction pump 188 facilitates passage of gas stream 178 with particulate material and/or droplets to be analyzed through the waveguide from top to bottom as shown in FIG. 5. It should be appreciated, however, that other arrangements for the positioning of the pump relative to the plasma flame may be employed in accordance with the invention. One such pump which is suitable for use in accordance with the present invention is a Penberthy jet pump. It should be appreciated, however, that other suction pumps are suitable for use in the invention. In a preferred embodiment, suction pump 188 is offset from sample flow tube 162 by a conduit 172 or the like as shown in FIG. 5. The sample gas 178 containing the sample therein exits the plasma torch subsystem 130 through exhaust 190.

In a preferred embodiment of the invention, a start-up system is included to facilitate initiation of the plasma and sustaining the plasma after it has been initiated. This may be accomplished using a start-up and sustainer tube 194 positioned in port 176 as shown in FIG. 5. Start-up and sustainer tube 194 has an end 196, which preferably is aligned with the inside wall 210a of waveguide 210 (as illustrated in FIG. 5). As further shown in FIG. 5, starter wire 198 is positioned inside start-up and sustainer tube 194 and is connected to a high voltage power supply 200, such as telsa coil. Starter wire 198 may be a thin tungsten wire or the like. In a preferred embodiment, start-up wire 198 is recessed a sufficient distance (inside tube 194) from the inside waveguide wall 210a to avoid directly coupling to the microwave power inside the waveguide. The high voltage power supply 200, e.g. >100 volts, is momentarily activated to create a discharge at the end of the start-up tube which provides the initial free electrons for start-up of the main microwave plasma torch.

The start-up and sustainer tube 194 preferably is connected to a source of auxiliary gas 202, such as argon. Regulation or control of auxiliary gas 202 may be accomplished using a valve 204 or the like that can be momentarily opened to facilitate the initiation of the main plasma torch.

Microwave source subsystem 140 is similar to the microwave source described above in connection with FIGS. 1–3. Microwave source subsystem 140 includes waveguide 210 having interior wall 210a and passageway 220 through the waveguide walls at the plasma location to allow for a clear flow of the gases through the plasma region. The aperture of the passageway 220 is less than $\frac{1}{4} \lambda_o$, where $\lambda_o$ is the free space wavelength of the microwave source power. Tubular structures 162 made of a microwave conducting material extend outward beyond the passageway 220 in both directions. These tubes 162 localize the gas flow through the plasma region and act as cutoff waveguides to prevent microwave leakage. The tubes are constructed from high temperature conductor material such as stainless steel or other suitable material. Microwave 210 preferably has a shorted waveguide end 212. Though not shown in FIG. 5, the waveguide could be tapered to increase plasma power density for increased robustness. Aperture 220 is lined with a perforated dielectric liner 214, which is transparent to microwaves and is capable of withstanding high temperatures. Exemplary materials suitable for use as a dielectric liner in accordance with the invention include, but are not limited to, boron nitride or alumina. The plasma 218 or gas flow passage is transverse to the waveguide direction for microwave power propagation 216, as shown in FIG. 5.

Spectrometer subsystem 150 is similar to that described above in connection with FIGS. 1–3. In particular, plasma 218 interacts with particulates, droplets, compounds and atoms in the sample gas by volatilizing and breaking compounds into their respective elements, thereby producing excited atoms. As the excited atoms decay, plasma light is emitted. The emitted plasma light which spans from the ultraviolet (180 nm) through near infrared (2000 nm) is transmitted by a fiber optic cable(s) 222 to a spectrometer, such as a Czerny Turner grating configuration. Fiber optic guides 222 may be embedded in the waveguide 210 and positioned to transmit the atomic emission light to a spectrometer system 150. For example and as shown in FIG. 5, fiber optic guides 222 may be positioned in the bottom wall of the waveguide and along the plasma flame outflow piping.

As mentioned above, system 120 further includes sample acquisition subsystem(s) 160. There are various ways in which to introduce a sample to be analyzed in system 120, and the subsystems illustrated in FIG. 5 are intended to be illustrative and not limiting. The sample acquisition techniques provide a continuous, real time flow of samples from the process material stream to be monitored. In one sample acquisition technique shown in FIG. 5, sufficiently small particulate and/or droplet samples can be introduced into the microwave plasma torch system 130 through sample insertion tube 192 positioned proximate to start-up and sustainer tube 194. A sample scraper 224 having a scraper arm 226 is utilized to scratch the surface of material stream 228 as it moves by and/or as scraper arm 226 is articulated. The resulting small particulates scraped from material stream 228 fall into a grinder or pulverizing machine 230 which converts the samples into a free powder. A free mesh strainer 232 preferably is employed to select a maximum particle size, e.g. <100 µm, which is dropped down or passes through feed tube 186 into the plasma torch subsystem 130. In this sample acquisition technique, gravity and gas flow 178 both act to entrain particles in the plasma flame 218.

In an alternative sample acquisition technique (also shown in FIG. 5), particulate and/or droplet samples can be introduced into microwave plasma torch system 130 using suction pump 188 to pull the samples through an extension 240 of suction tube 184 and into the main gas flow. A sample impactor 236 is positioned near material stream 234 and suction input 238 to the plasma torch subsystem 130. Sample impactor 236 creates and knocks small particles or droplets from material stream 234 that are subsequently entrained in the gas flow stream 178 through the plasma torch subsystem 130 by the suction action of pump 188 and/or gravity. The sample impactor 238 could be a repetitively pulsed rod in a solenoid, a repetitively pulsed high pressure gas jet, an electromagnetic pulse such as from a laser, or the like. A valve 180 positioned near the feed of gas flow 178 may be utilized to control the degree of suction that is achieved in the suction tube 184 for sample acquisition. Preferably, large particle trap 182 is positioned below suction tube 184, thereby allowing large particles to fall out of or be removed from the gas flow prior to passage through plasma flame 218.

It should be appreciated that the present invention is not limited to the sample acquisition techniques shown in FIG. 5. Other sample acquisition techniques are suitable for use in accordance with the present invention. While not intended to be construed as limiting, other sample acquisition techniques include the use of a high energy laser beam or electric spark discharges to ablate or fracture samples from the process stream into the plasma torch.

The microwave plasma torch provided by the embodiment of the present invention illustrated in FIG. 5 facilitates absolute calibration for the mass of each element species passing through the plasma flame. Absolute calibration is achieved by dropping a predetermined amount of powder of known element masses through the sample insertion tube. The short vertical drop insures that all the calibration mass passes through the flame. The fiber optic guides positioned along the flow of the plasma flame allow the determination of the rate of mass flow by time of flight measurement of the calibration mass transient through the flame. Any unvolatilized calibration particulates are collected on the clean out port flange and can be weighed to account for the fraction of the calibration mass that was not volatilized.

The design of the microwave plasma monitoring system in accordance with the present invention is very robust and allows the plasma torch to be positioned in a high temperature environment very near or proximate to the process stream to be monitored, thereby minimizing sample transport losses. Additionally, it is not necessary that the plasma torch be located below the monitored process stream. A sample acquisition subsystem that lifts the sample a short distance to drop the sample through the plasma flame may be readily adapted for use in the present invention.

Example 1

A microwave plasma and waveguide torch device as shown in FIG. 4 was constructed of refractory materials and was implemented as part of the furnace exhaust duct to sample high temperature, greater than 500° C., undiluted exhaust gases exiting a 1 MW DC graphite electrode plasma arc furnace (Mark II furnace). The results proved the device to be a robust gas excitation device for sensitive in situ atomic emission spectroscopy (in the part per billion range) of metals entrained in the exhaust emissions. The microwave plasma device for atomic emission spectroscopy of the furnace emissions used a 1.5 kW, 2.45 GHz magnetron source. The device was mounted to the side of the Mark II furnace exhaust duct as shown in FIG. 4 such that the exhaust pick-up pipe was about 1 meter from the inside furnace wall.

The pick-off tube directed undiluted hot furnace exhaust directly into the microwave plasma well upstream of the scrubbers. By sampling upstream of the scrubbers, the sensitivity to actual emissions into the air is increased by the efficiency of the scrubbers to remove metals. The maximum temperature measured with a thermocouple installed on the exhaust pick-off pipe was 660° C. It was observed that plasma robustness improved with temperature. There was no evidence of the plasma extinguishing with the maximum particulate loadings encountered during soil feeding into Mark II.

The plasma was induced inside a shorted graphite waveguide which also propagated the microwave power to the plasma from the magnetron. The waveguide internal cross-sectional dimensions were 7.21×3.40 cm (WR284 band) with a 3.5 cm diameter hole through the wider sides of the guide ¼ wavelength back from the short. This hole was lined with a boron nitride tube with an internal diameter of 2.86 cm which confined the plasma and gas flow through the waveguide.

The furnace exhaust stream was intercepted by a 2.86 cm diameter stainless steel tube which was bent into the center of the furnace exhaust duct. The total length of this exhaust pick off tube was 48 cm. A Penberthy jet pump was used as a suction pump downstream of the plasma to insure an adequate gas flow was maintained through the waveguide. The nominal gas flow through the waveguide was in the range of 10–30 l/m (20–60 scfh). After passing through the plasma, the exhaust gas was returned to the furnace exhaust duct.

An alumina dielectric tube penetrated the exhaust pick off tube to the waveguide wall, centered in the hole through the guide. The end of this alumina tube provided a thermal source of electrons when heated by the plasma to keep the plasma centered in the gas flow through the guide. This tube also provided a way in which to introduce a starter and calibration samples into the plasma.

Fused quartz fiber guides with high temperature gold cladding from Fiberguide Industries were utilized to transmit the plasma light to the spectrometers. These fibers were embedded inside the graphite waveguide wall in an alumina tube and could be readily replaced during furnace operation. The fibers penetrated the boron nitride liner so that the fiber ends were in close proximity to the inside wall of the boron nitride tube. The radiated plasma heat and the rapid gas flow kept the viewing ends of theses fibers clean. The furnace was run for about 4 days continuously at a maximum temperature of about 1710° C. Ten 40 pound bags of clean Idaho Falls soil containing a 10% mix by weight of calcium carbonate were loaded into the furnace, melted and poured by the middle of the fourth day. The microwave plasma was on for two days of continuous operation, including the soil loading campaign. Only one fiber of the three used was observed to have degraded light transmission after two days of operation.

Two spectrometers were used to analyze the plasma light in the 183–690 nm wavelength range. A low resolution Ocean Optics Model SD1000 instrument provided complete instantaneous surveys of this entire wavelength range on time scales of less than one second with about 1 nm resolution. High resolution spectra were obtained with a SPEX Model THR-640, 0.64 m Czerny-Turner spectrometer having a 2400 g/mm grating and a 512 silicon diode array from Princeton Instruments. The high resolution spectrometer had a resolution of approximately 0.01 nm and an instantaneous wavelength range of approximately 6.5 nm. Through instantaneous spectra as fast as once every 17 ms could be obtained with a high resolution spectrometer system, data was generally acquired once every 0.5 seconds during the furnace run to conserve computer storage memory.

Laboratory tests of this microwave plasma device have demonstrated plasma robustness and high sensitivity to trace elements. Using nitrogen as the gas flow medium (nitrogen is the purge gas for Mark II) and SPEX calibration powered mixes inserted directly into the plasma flame, detection limits for the metals: Ag, Ba, Be, Cd, Ni, Sb, Cr, Pb, Hg and As were determined to range from 0.01 ppb for Ag to 1 ppb for As. In addition, plasma temperatures in the range of 5000° to 6000° K. were spectroscopically determined, a range which is sufficiently hot to vaporize particulate, decompose oxides, and excite all metal species in the exhaust. For example, when refractory zirconium oxide particles were introduced atomic zirconium was observed in the emission spectrum.

Figure 6:
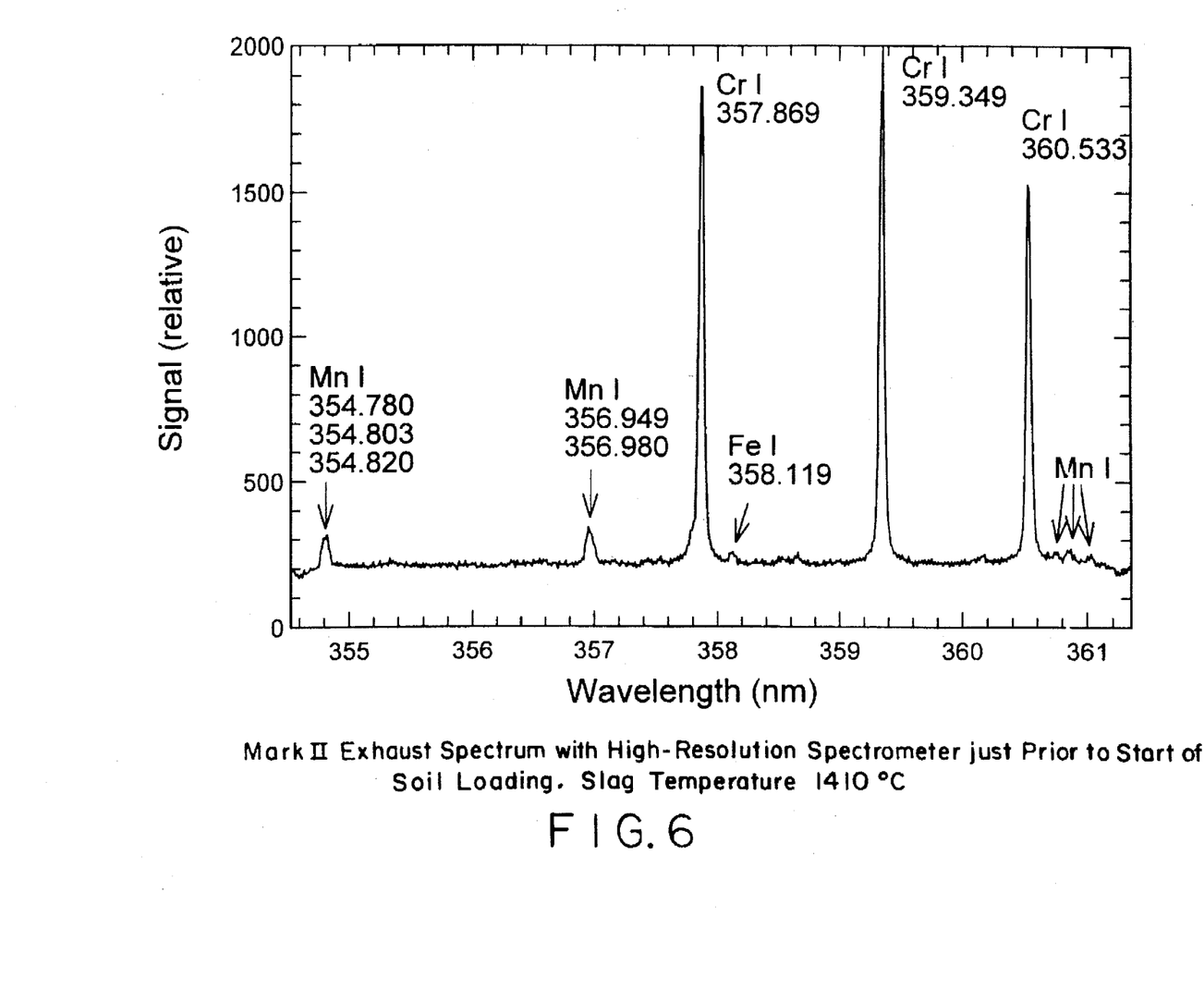
FIG. 6 is an exhaust spectrum of off-gases from a DC graphite electrode plasma arc furnace (Mark II furnace) using a high-resolution spectrometer just prior to initiation of soil loading in accordance with the embodiment of the invention illustrated in FIG. 4.

A representative exhaust spectrum taken with the high resolution spectrometer just prior to soil loading (slag temperature at about 1410° C.) is illustrated in FIG. 6. The spectrometer was tuned to a region of the spectrum where prominent lines of chromium are known to emit. Chromium was the only hazardous metal in the list given above which was continually present in the furnace emissions of this run. Other metals evident in the furnace emissions just prior to soil loading were manganese and iron. The relative ratios of these metals emissions evolved during the 48 hour monitoring period as the chemistry of the slag changed. All these metals were present in the original soil fill of the hearth.

While these signals levels were not absolutely calibrated, preliminary calibrations of this device with well characterized soil dust prior to furnace turn on have approximately reproduced the threshold detection limit for chromium (0.3 ppb for the 359.349 nm transition) established in the laboratory with SPEX powder. Assuming the plasma properties did not changed significantly with temperature, then an order of magnitude estimate for the concentrations corresponding to the chromium signals shown in FIG. 6 is in the 3–30 ppb range.

As further illustrated in FIG. 6, there was no interference from $N_2^+$ or CN molecule which was observed in the laboratory tests of this device in this wavelength range. This was unexpected since Mark II is arcing to graphite electrodes in a nitrogen purge, a condition that would seem likely to create the gas matrix for these interfering species to be present in the microwave plasma. The relatively clean background observed in the emission spectrum of actual furnace exhaust gas suggests that laboratory sensitivities may be achieved in situ.

Figure 7:
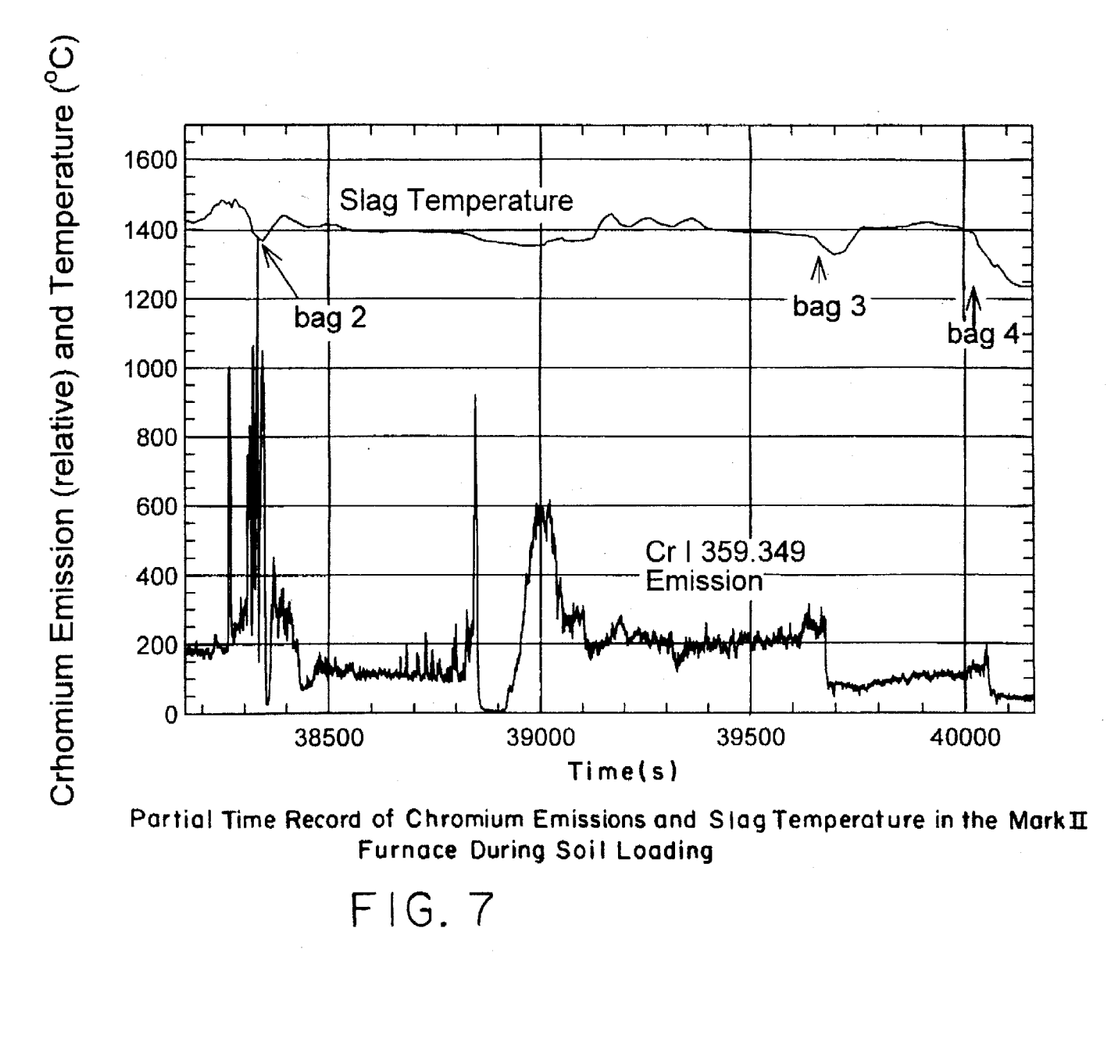
FIG. 7 is a partial time record of chromium emissions and slag temperature in a DC graphite electrode plasma arc furnace (Mark II furnace) during soil loading in accordance with the embodiment of the invention illustrated in FIG. 4.

FIG. 7 illustrates the record of the real time chromium emissions and slag temperatures during a 33 minute period when three of the soil bags were dropped into the hearth. The chromium signal estimated to be less relative levels, but the peak levels are estimated to be less than 100 ppb. The chromium emissions first increased rapidly when a soil bag was dropped into the melt, and was followed by a sudden decrease as the slag is cooled slightly by the new soil. There was also bunting and decrease in chromium emissions between bags 2 and 3 which could be related to the assimilation of the first few bags into the slag and adjustment of the arc length. FIG. 7 further illustrates the capability for rapid real time monitoring of hazardous metals emissions which could be used for furnace control to minimize air pollution.

The microwave plasma device according to the present invention promises to be a sensitive and comprehensive monitor for all metals in whatever form or compound that they exist in the furnace exhaust.

It should be appreciated by those skilled in the art that the specific embodiments disclosed above may readily be utilized as a basis for modifying or designing other methods or structures for carrying out the same purpose of the present invention. It should also be realized by those skilled in the art that such equivalent constructions do not depart from the spirit and scope of the invention as set forth in the appended claims.

What is claimed is:

1. An apparatus for analyzing the composition of a sample, comprising:

a shorted waveguide made of a microwave conductive material using refractory material communicating with a source of microwave energy to generate plasma, the waveguide including an aperture for the passage of the sample to be analyzed;

sample flow means connected to the waveguide such that the aperture in the waveguide is aligned with the sample flow means;

means for adjusting a passage rate of the sample to be analyzed through the shorted waveguide; and a spectrometer connected to receive light from the plasma.

2. The apparatus of claim 1 further including a source of sample gas for entraining the sample to be analyzed in the sample gas, wherein the sample gas and the sample entrained in the sample gas flow through the shorted waveguide.

3. The apparatus of claim 1 further including means for initiating the plasma.

4. The apparatus of claim 3 wherein the means for initiating the plasma comprises:

a tube connected to the waveguide such that an end of the tube is positioned to provide the initial plasma within the waveguide;

a wire positioned within the tube; and a power supply connected to the wire.

5. The apparatus of claim 4 wherein the tube is formed of a dielectric material.

6. The apparatus of claim 5 wherein the dielectric material is alumina.

7. The apparatus of claim 5 wherein the dielectric material is boron nitride.

8. The apparatus of claim 4 wherein the wire is formed of tungsten.

9. The apparatus of claim 4 wherein the power supply is a telsa coil.

10. The apparatus of claim 4 wherein the tube is formed of alumina or boron nitride, the wire is formed of tungsten and the power supply is a telsa coil.

11. The apparatus of claim 4 further including a source of auxiliary gas connected to provide auxiliary gas to the tube.

12. The apparatus of claim 11 wherein the auxiliary gas is argon.

13. The apparatus of claim 1 further including sample acquisition means for acquiring the sample to be analyzed.

14. The apparatus of claim 13 wherein the sample acquisition means comprises:
a scraper having a scraper arm;
a grinder in a predetermined position relative to the scraper; and
means for introducing the sample to be analyzed into the sample flow means.

15. The apparatus of claim 14 further including a strainer connected to the grinder and connected to the means for introducing the sample such that the strainer receives the sample from the grinder and strains the sample prior to introduction into the means for introducing the sample.

16. The apparatus of claim 14 wherein the means for introducing the sample includes a feed tube connected to the grinder and the sample flow means.

17. The apparatus of claim 16 wherein the means for introducing the sample further includes a sample insertion tube connected to the sample flow means and connected to the feed tube.

18. The apparatus of claim 13 wherein the sample acquisition means comprises;
a sample impactor positioned proximate to a sample to be analyzed; and
means for collecting and feeding the sample to the sample flow means.

19. The apparatus of claim 18 wherein the sample impactor is a rod in a solenoid.

20. The apparatus of claim 18 wherein the sample impactor is a high pressure gas jet.

21. The apparatus of claim 1 wherein the means for adjusting the passage rate of the sample includes a suction pump in a predetermined position relative to the sample flow means and the shorted waveguide.

22. The apparatus of claim 21 wherein the suction pump is positioned downstream of the waveguide such that the suction pump pulls the gas flow having the sample to be analyzed therein through the waveguide.

23. The apparatus of claim 1 wherein the source of microwave energy has an output of greater than 500 Watts.

24. The apparatus of claim 23 wherein the microwave source is a magnetron.

25. The apparatus of claim 1 wherein the apparatus operates at about atmospheric pressure.

26. The apparatus of claim 1 wherein the waveguide is made of graphite.

27. The apparatus of claim 1 wherein the sample passage through the waveguide is lined with a perforated dielectric liner.

28. A method for analyzing the composition of a sample of a process stream, comprising:
establishing a plasma in an aperture of a shorted refractory waveguide;
establishing an adjustable gas flow through the waveguide;
exposing the sample to be analyzed and the gas to the plasma;
transmitting emitted plasma light to a spectrometer;
dispersing the emitted light with a spectrometer;
detecting the dispersed light with a detector; and
analyzing the detected light with a computer to determine the composition of the sample.

29. The method of claim 28 wherein the plasma is in a downward arrangement.

30. The method of claim 29 further comprising calibrating emission levels for quantitative measurements with a calibration source, the step of calibrating comprising:
injecting by gravity an element to be analyzed from a known matrix of elements;
exciting the injected element in the plasma;
detecting emitted plasma light;
accounting for any mass of the calibration sample that was not excited by the plasma; and
controlling the spectrometer tuning and the calibration source with a computer that processes data received from the detector and accounts for any of the unexcited mass of the calibration sample.

31. An apparatus for analyzing the composition of a sample, comprising:
a shorted waveguide made of a microwave conductive material using refractory material communicating with a source of microwave energy to generate plasma, the waveguide including an aperture for the passage of the sample to be analyzed;
a sample flow tube connected to the waveguide such that the aperture in the waveguide is aligned with the sample flow tube, the sample flow tube positioned to receive the sample to be analyzed;
a suction pump connected to the sample flow tube for adjusting a passage rate of the sample to be analyzed through the shorted waveguide; and
a spectrometer connected to receive light from the plasma.

32. The apparatus of claim 31 wherein the sample flow tube intercepts furnace exhaust such that a portion of furnace exhaust gas enters the sample flow tube and passes through the plasma.

33. The apparatus of claim 32 wherein the sample flow tube is angled such that an entrance of the sample flow tube extends into the furnace exhaust.

34. The apparatus of claim 33 wherein the suction pump is positioned downstream of the plasma.

35. The apparatus of claim 34 wherein the sample flow tube includes an exhaust return portion attached to an exit of the suction pump, the exhaust return portion positioned to reintroduce the sample into the furnace exhaust.

36. The apparatus of claim 35 further including a source of electrons for maintaining plasma position in the gas flow.

37. The apparatus of claim 35 wherein the source of electrons includes an alumina tube.

38. An apparatus for analyzing the composition of a sample, comprising:
a shorted waveguide made of a microwave conductive material using refractory material communicating with a source of microwave energy to generate plasma, the waveguide including an aperture for the passage of the sample to be analyzed;
a sample flow tube connected to the waveguide such that the aperture in the waveguide is aligned with at least a portion of the sample flow tube, the sample flow tube positioned to receive a source of sample gas and the sample to be analyzed;
sample acquisition means for acquiring the sample to be analyzed, the sample acquisition means connected to the sample flow tube;
a suction pump connected to the sample flow tube for adjusting a passage rate of the sample to be analyzed through the shorted waveguide; and
a spectrometer connected to receive light from the plasma.

39. The apparatus of claim 38 wherein the suction pump is positioned downstream of the plasma.

40. The apparatus of claim 39 wherein the suction pump is offset to one side of an axis of the plasma.

41. The apparatus of claim 40 further including a debris trap positioned downstream of the plasma.

42. The apparatus of claim 40 wherein the sample flow tube includes an exhaust portion attached to an exit of the suction pump.

43. The apparatus of claim 38 further including means for initiating the plasma comprising:

a tube connected to the waveguide such that an end of the tube is positioned to provide the initial plasma within the waveguide;

a wire positioned within the tube; and a power supply connected to the wire.

44. The apparatus of claim 38 wherein the sample acquisition means comprises:

a scraper having a scraper arm;

a grinder in a predetermined position relative to the scraper; and means for introducing the sample to be analyzed into the sample flow tube.

45. The apparatus of claim 44 wherein the means for introducing the sample includes a feed tube connected to the grinder and the sample flow tube.

46. The apparatus of claim 45 wherein the means for introducing the sample further includes a sample insertion tube connected to the sample flow tube and connected to the feed tube.

47. The apparatus of claim 38 wherein the sample acquisition means comprises;

a sample impactor positioned proximate to a sample to be analyzed; and means for collecting and feeding the sample to the sample flow tube.

* * * * *

UNITED STATES PATENT AND TRADEMARK OFFICE
CERTIFICATE OF CORRECTION

PATENT NO. : 5,671,045

DATED : September 23, 1997

INVENTOR(S) : Paul P. Woskov, Daniel R. Cohn, Charles H. Titus and Jeffrey E. Surma It is certified that error appears in the above-identified patent and that said Letters Patent is hereby corrected as shown below:

On the cover page of the patent, following "[73] Assignee: Massachusetts Institute of Technology, Cambridge, Mass.", insert --; Battelle Memorial Institute, Richland, Wash.--.

Column 5, line 5: please delete "cream"; and insert therefor --create--.

Column 5, line 25: please delete "utilities"; and insert therefor --utilizes--.

Column 9, line 35: please delete "pan"; and insert therefor --part--.

Column 9, line 39: please delete "are"; and insert therefor --arc--.

Column 9, line 45: please delete "pan"; and insert therefor --part--.

Column 10, line 67: please delete "an∨ and insert therefor --and/or--.

Column 12, line 66: please delete the first use of "free"; and insert therefor --fine--.

UNITED STATES PATENT AND TRADEMARK OFFICE
CERTIFICATE OF CORRECTION

PATENT NO. : 5,671,045

DATED : September 23, 1997

INVENTOR(S) : Paul P. Woskov, Daniel R. Cohn, Charles H. Titus and Jeffrey E. Surma It is certified that error appears in the above-identified patent and that said Letters Patent is hereby corrected as shown below:

Column 12, line 66: please delete the second use of "free"; and insert therefor --fine--.

Column 16, line 2: please delete "bunting"; and insert therefor --bursting--.

Signed and Sealed this

Twenty-eighth Day of April, 1998

Attest:

Attesting Officer

BRUCE LEHMAN

Commissioner of Patents and Trademarks